United States Patent [19]

Samuels

[11] Patent Number: 5,047,041
[45] Date of Patent: Sep. 10, 1991

[54] SURGICAL APPARATUS FOR THE EXCISION OF VEIN VALVES IN SITU

[76] Inventor: Peter B. Samuels, 14708 Sutton St., Sherman Oaks, Calif. 91403

[21] Appl. No.: 497,840

[22] Filed: Mar. 23, 1990

Related U.S. Application Data

[63] Continuation of Ser. No. 397,640, Aug. 22, 1989, abandoned, which is a continuation of Ser. No. 212,772, Jun. 29, 1988, abandoned.

[51] Int. Cl.$^5$ ............................................. A61B 17/32
[52] U.S. Cl. .................................................. 606/159
[58] Field of Search ................ 606/159, 167; 128/751, 128/753, 754

[56] References Cited

U.S. PATENT DOCUMENTS 4,785,826  11/1988  Ward .................................... 128/754
4,952,215   8/1990  Ouriel et al. ........................ 606/159

FOREIGN PATENT DOCUMENTS 6513901  5/1966  Netherlands ...................... 128/751

OTHER PUBLICATIONS

Le Maitre, "In Situ Bypass Grafting", Vascutech, Inc. (1987).

Primary Examiner—Michael H. Thaler
Attorney, Agent, or Firm—Rockey and Rifkin

[57] ABSTRACT

An improved surgical device for cutting and removing venous valves is disclosed. The valve cutter is provided with a circular cutting head and a dilating segment affixed to a cable or wire. The circular cutting edge promotes engagement of the valve cusps and does not require orientation within the vein during surgery. A serrated or toothed cutting edge further promotes engagement of the valve leaflets and helps to prevent slippage of the valve leaflet pairs. The serrated cutting edge is tapered inward to prevent trauma to or tearing of the venous wall.

2 Claims, 1 Drawing Sheet

SURGICAL APPARATUS FOR THE EXCISION OF VEIN VALVES IN SITU

This is a continuation of Ser. No. 07/397,640 filed Aug. 22, 1989 now abandoned which is a continuation of Ser. No. 07/212,772 filed in June 29, 1988 now abandoned.

BACKGROUND AND SUMMARY OF THE INVENTION

This invention relates to a surgical device for inactivating venous valve cusps for use in the preparation of a vein for in situ vein bypass.

Autogenous venous bypass is a popular method for the surgical treatment of femoropopliteal arterial obstruction. Generally, the procedure involves the use of the long saphenous vein, a vein passing up the leg from the ankle to the groin, to form a conduit around a blocked artery. To use this easily accessible vein as a bypass conduit, it is first necessary to overcome the barrier imposed by the vein valves. In particular, the saphenous vein is intersected by three to seven valves. The valves allow blood to pass upwards toward the heart and prevent blood from flowing in reverse while one is in an upright position. Deactivation of the venous valves is required to permit use of the vein as an arterial bypass conduit.

Deactivation of the venous valves was first accomplished by severing and removing the saphenous vein from the body, reversing the vein, and rejoining the vein to an artery at points above and below the area of arterial blockage. Arterial blood flows past the valves in an unobstructed manner because the valves are redirected by reversing the vein. However, there are many potential surgical problems encountered with reversed-vein bypassing procedures, including twisting and compressing of the body of the vein during the vein removal and reversal process. There are also problems in anastomosising or grafting the smaller diameter of the reversed vein to the larger diameter, thicker portion of the artery, and vice versa. Moreover, the preservation of the highly sensitive endothelial layer of the vein conduit is of utmost importance to successful bypass results and requires careful attention and surgical procedures to ensure such preservation.

Alternative in situ vein bypass procedures were developed in response to the problems encountered with reversed-vein bypass methodology. In situ vein bypass refers to the use of a vein as it lies anatomically within the body, i.e., without removal and reversal of the vein. There are many advantages associated with the in situ method. For example, the potential for twisting of the vein in situ is greatly reduced. Because the vein is not reversed, the larger end of the vein is attached to the larger portion of the femoral artery and the smaller distal end of the vein is attached to the smaller distal portion of the artery. The anastomosis is therefore easier to construct and, because the vein is tapered from entrance to outlet, the resultant conduit is hemodynamically sound, resulting in improved blood flow. Moreover, by utilizing the vein in situ, minimal vein dissection occurs and the endothelial lining of the vein can be better preserved.

The most critical step in the in situ procedure is producing valve incompetence within the vein. To date, the only certain way of inactivating the valve cusps or leaflet pairs is by complete excision of the valve cusps. Existing methods for accomplishing valve excision involve pulling or pushing a valve cutter or valvulotome down through the inside of a vein to excise vein leaflets. Before the cutting device is drawn through the vein, the vein is distended or pressurized with fluid to close the valves. This can be accomplished by grafting the top of the vein to the artery so that pressurized arterial blood passes into the vein. Alternatively, a saline solution can be pumped through a canulla into the top of the vein lumen as the pressurizing fluid. The blood or saline descends through and distends the vein, causing the first pair of valve leaflets or cusps to stretch across the vein and to close tightly. The valve cutter is then pulled through the tightly closed valve leaflets, thereby destroying or excising the venous valve leaflets. The pressurized fluid passes through the destroyed valve, causing the next valve to close. This pressurization and cutting procedure is carried out in succession for each valve leaflet pair. When all the valves are destroyed, the vein becomes a workable arterial bypass conduit. This procedure and various prior art cutting devices are described in Samuels, Plested, Haberfeld, Cincotti, and Brown, *The American Surgeon*, 34, 2, February, 1968, 122-130 and Leather, Shah, Corsin and Carmody, *Journal of Vascular Surgery*, 1, 1, 113-123, January, 1984. These prior devices, however, are quite difficult to manipulate and control and often cause significant trauma and damage to the vein.

Other, more recent devices for disabling valve cusps are known. For example, U.S. Pat. No. 4,655,217, describes a valve cutting device wherein retractable wire hooks are positioned within a flexible guide tube. When the wire hooks are moved from their retracted position within the tube to an extended position toward the vein wall, valve cusps are entrapped and disabled upon pulling the hooks down through the valve cusps.

The valve cutter disclosed in U.S. Pat. No. 4,493,321 utilizes a reversed arrowhead design for cutting valve leaflets. The device includes a rounded leading device to prevent damage to the vein wall, a straight cutting blade positioned between two protective supports, and a flexible rod connecting the leader to the cutting blade. The use of this device requires continuous controlled orientation of the straight cutting blade within the vein to prevent the cutting blade from catching and tearing the orifice wall of a venous branch and to ensure efficient engagement and incision of both valve leaflets. The device is useful only for those portions of the saphenous vein above the knee. The removal of valves in the smaller distal portions of the vein extending below the knee requires a different cutter device.

Thus, there is a need for an improved, self-centering, self-orienting, valvulotome.

Accordingly, an object of this invention is to provide a new and improved valvulotome.

A more particular object is to provide a valve cutter that does not require orientation within the vein to ensure contact with and intersection of the apposed valve leaflet pair.

Another object is to provide a cutting member that will engage leaflets without slipping away from the leaflet during excision.

Yet another object of this invention is to provide a valvulotome having a cutting edge that will only contact and cut valve leaflets and will not impinge on the wall of the vein or catch in the openings of vein branches.

In keeping with one aspect of this invention, a circular cutting head is affixed to a cable or wire and is, preferably, preceded by a dilating segment also affixed to the wire. The dilating segment straightens out the vein and centers the cutting head within the vein so that the cutting head does not impinge on the vein walls or enter a venous branch. The circular cutting edge permits engagement of the valve cusps without separate, continuous surgical orientation of the cutting device within the vein. A serrated or toothed cutting edge further promotes engagement of the valve leaflets and also helps to prevent slippage of the valve leaflet pairs. The serrated cutting edge is tapered inward to prevent trauma to or tearing of the venous wall.

In use, the cutting head, centering device, and cable are inserted into the saphenous vein at the distal anastomotic site or through a tributary vein. The cutting head and dilating or centering segment are inserted up through the vein and successive valve cusps to the proximal anastomatic site. The vein is pressurized with arterial blood or other fluid to close the first valve cusp. The cutting device is then drawn down through the tightly closed valve leaflet pairs. As the device is drawn, the lips of the valve leaflets are guided into the sharpened arcuate grooves of the toothed cutting edge. A slight pull on the device cuts the valve leaflets. This procedure is repeated as the valvulotome is withdrawn down the length of the vein until all valves have been rendered incompetent. Thus, the vein is prepared in situ for use as an arterial bypass conduit.

BRIEF DESCRIPTION OF THE DRAWINGS

The above mentioned and other features of this invention and the manner of obtaining them will become more apparent, and the invention itself will be best understood by reference to the following description of an embodiment of the invention taken in conjunction with the accompanying drawings, in which.

DETAILED DESCRIPTION

Figure 1:
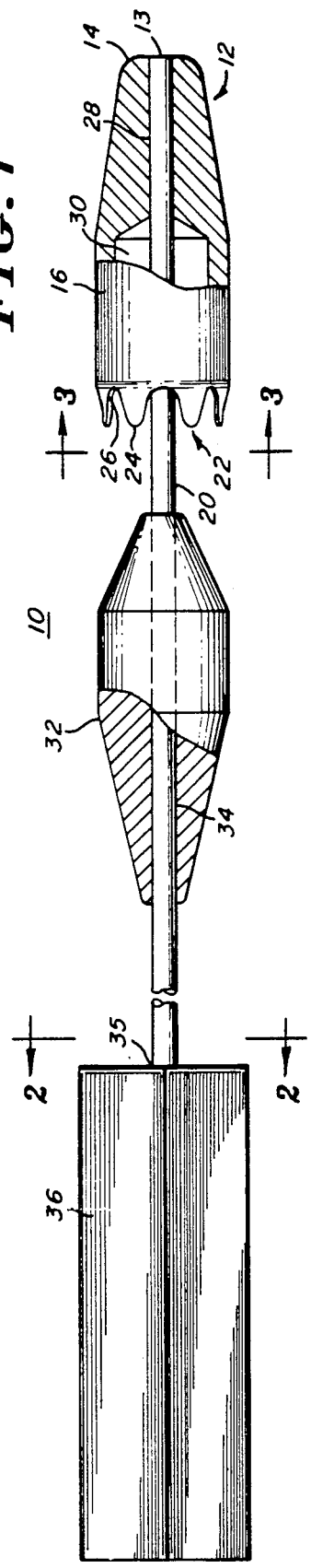
FIG. 1 is a side view of one embodiment of the present invention.

FIG. 1 is a side view of a preferred embodiment of the valvulotome 10 of the present invention. The valvulotome 10 includes a cutting head 12, a centering or dilating segment 32, and a flexible guide cable 20. The cable 20 moves the cutting head 12 and dilating segment 32 axially through the vein in either direction. The centering or dilating segment 32 straightens the vein and centers the cutting head 12 within the vein as the cutting head 12 is drawn through a vein.

Figure 4:
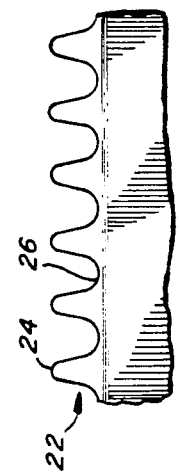
FIG. 4 is a side elevational view of a cutting edge made in accordance with this invention.
Figure 3:
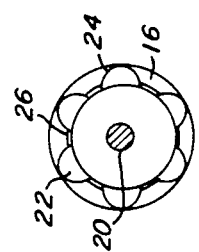
FIG. 3 is a cross-sectional view of the tooth and groove cutting edge taken along line 4—4 in FIG. 2.

Cutting head 12 has a front end or section 14 and a rear, hollow, cylindrical end or section 16. The front end 14 is preferably closed and tapered to a smooth bullet shape for easy passage within a vein. Rear section 16 includes a cutting edge 22. The cutting edge 22 is circular and is serrated with a plurality of teeth 24 and grooves 26. Rear section 16, including cutting edge 22, is of sufficient taper to minimize contact with the inner walls of the vein. The inward taper of rear section 16 is further illustrated in FIG. 3. Each tooth 24 consists of a rounded outer edge designed to guide the valve leaflets into grooves 26. The grooves 26 have sharpened edges such that when the valve leaflets are guided into the grooves 26 by the teeth, they are severed by the sharpened edge. The arrangement of the teeth 21 and grooves 26 enhances excision or destruction of the leaflets by minimizing slippage of the leaflets off the cutting edge 22. The continuous tooth and grooved cutting edge 22 is also shown in FIGS. 3 and 4.

The centering or dilating segment 32 straightens the valvulotome 10 within the vein, thereby minimizing the danger of tearing a vein wall or of engaging and tearing the orifice of a branch vein. The centering or dilating segment 32 further centers the cutting edge 22 of the cutting head 12 on the valve leaflets so that the valve leaflets will be more efficiently severed. The centering or dilating segment 32 is of sufficient taper to facilitate its passage through the vein. In the embodiment of FIG. 1, centering segment 32 is an ovoid body with a longitudinal central bore for receiving and connecting cable 20 to the dilating segment 32.

Figure 2:
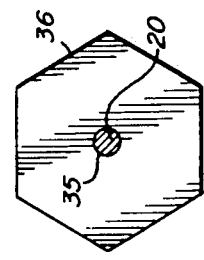
FIG. 2 is a cross-sectional view of the anchoring means taken along line 3—3 in FIG. 2.

Cable 20 connects cutting head 12 and segment 32 and further provides a means for moving the combination of valvulotome elements through the vein. At its one end 13, cable 20 is connected to the cutting head 12. At its other end 35, cable 20 may be connected to anchoring means 36 as illustrated in FIGS. 1 and 2. In the preferred embodiment of FIG. 1, the front end 14 of cutting head 12 has a longitudinal central bore 28 for receiving and anchoring cable 20. Rear end 16 is hollow and forms a continuous circumferential cutting edge surrounding cable 20, as further shown in FIG. 3. Centering segment 32 is positioned next to the rear section 16 of cutting head 12.

The materials used for construction of the valvulotome 10 may be of any suitable surgical materials for the purposes indicated and preferably are inert and nontoxic. The valvulotome 10 may be of any suitable diameter for passage through a vein, functioning equally well within any diameter of a vein, including the smaller-diameter, distal portion of the vein located below the knee.

Figure 5:
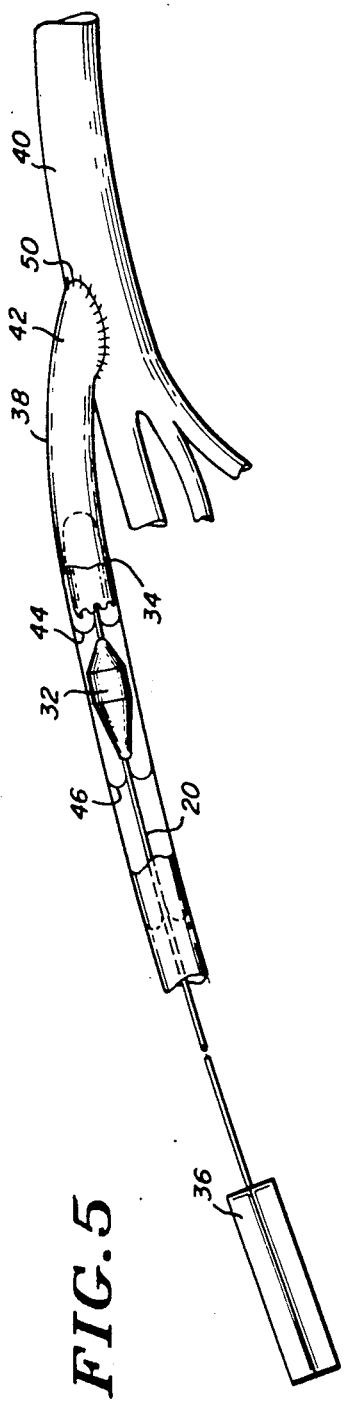
FIG. 5 illustrates the invention as used within a vein.

FIG. 5 illustrates the use of the cutting device in situ. A vein 38 is grafted or anastomosised in situ to an artery 40. The vein is pressurized by arterial blood flow into the vein, thereby causing the first valve leaflet pairs 44 to close tightly. It will be observed from FIG. 5 that the valvulotome 10 is inserted into a distal portion of the vein 38 and pushed up through the vein to the proximal portion of the vein 42 near the grafting site 50. Cable 20 is then drawn down through the vein such that centering segment 32 passes through the closed valve leaflets, centering the valvulotome 10 and cutting head 12 within the vein and further centering the cutting edge 22 on the valve leaflets 44. Upon engagement of the valve leaflets 44 with cutting edge 22, cable 20 is tugged or pulled, thereby cutting and/or disabling valve leaflets 44 from vein 38. Arterial blood flows through the excised valve causing the next valve leaflet pair 46 to close tightly. The centering and cutting procedure is repeated for valve leaflet pair 46 and successive valve cusps until all valves are rendered incompetent. The vein can then be used as an in situ arterial bypass conduit.

While the principles of the invention have been described above in connection with a specific embodiment thereof, it is to be understood that various changes in form and detail can be made without departing from the true spirit and scope of the claimed invention.

I claim:

1. A device for cutting venous valve leaflets, comprising:
   (a) a cylindrical cutting head having a front end and a hollow rear end, said rear end having rearwardly projecting, inwardly tapered, guide teeth separating several self-locating cutting grooves adapted to engage and sever the valve leaflets;
   (b) cable means secured to the cutting head and extending from said hollow rear end for permitting insertion and withdrawal of the cutting head within a vein, said guide teeth causing the cutting grooves properly to engage and sever the valve leaflets as the cutting head moves past the valve leaflets during its withdrawal from the vein; and
   (c) a centering segment secured to said cable means adjacent to said rear end of the cutting head for centering the cutting head and for preventing it from engaging side branches of the vein.

2. The invention of claim 1 wherein said centering segment is an ovoid body.

* * * * *